(12) United States Patent
Sugihara et al.

(10) Patent No.: US 7,442,387 B2
(45) Date of Patent: Oct. 28, 2008

(54) PHARMACEUTICAL COMPOSITION FOR CONTROLLED RELEASE OF ACTIVE SUBSTANCES AND MANUFACTURING METHOD THEREOF

(75) Inventors: Akio Sugihara, Shizuoka (JP); Kazuhiro Sako, Shizuoka (JP); Toyohiro Sawada, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 102 days.

(21) Appl. No.: 10/746,562

(22) Filed: Dec. 23, 2003

(65) Prior Publication Data
US 2004/0213845 A1 Oct. 28, 2004

Related U.S. Application Data

(60) Provisional application No. 60/453,046, filed on Mar. 6, 2003.

(51) Int. Cl.
| | |
|---|---|
| A61K 9/22 | (2006.01) |
| A61K 9/20 | (2006.01) |
| A61K 9/26 | (2006.01) |
| A61K 9/32 | (2006.01) |
| A61K 9/14 | (2006.01) |
| A61K 33/26 | (2006.01) |
| A61K 31/295 | (2006.01) |
| A01N 55/02 | (2006.01) |
| A01N 59/16 | (2006.01) |

(52) U.S. Cl. .................. 424/468; 424/464; 424/469; 424/482; 424/486; 424/647; 514/502
(58) Field of Classification Search ............... 424/647, 424/464, 468, 469, 482, 486; 514/502
See application file for complete search history.

(56) References Cited
U.S. PATENT DOCUMENTS
4,810,502 A 3/1989 Ayer et al.
5,547,683 A 8/1996 Yano et al.
5,945,125 A * 8/1999 Kim ........................... 424/473
6,368,626 B1 4/2002 Bhatt et al.
6,419,954 B1 7/2002 Chu et al.
6,488,963 B1 12/2002 McGinity et al.
6,562,375 B1 * 5/2003 Sako et al. .................. 424/486
2002/0028240 A1 3/2002 Sawada et al.

FOREIGN PATENT DOCUMENTS
| | | |
|---|---|---|
| JP | 11-193230 | 7/1999 |
| JP | 11-335268 | 7/1999 |
| WO | WO 96/32097 | * 10/1996 |
| WO | WO 99/06045 | * 2/1999 |

OTHER PUBLICATIONS

Taiwan Patent Office; Search Report.

* cited by examiner

*Primary Examiner*—Johann Richter
*Assistant Examiner*—Ernst Arnold
(74) *Attorney, Agent, or Firm*—Townsend and Townsend and Crew LLP

(57) ABSTRACT

The present invention pertains to a sized product, which contains a drug, polyethylene oxide with a molecular weight of 2,000,000 or higher, and a specific size controlling agent for polyethylene oxide (substance with the appropriate plasticity and binding force) and wherein at least the above-mentioned specific size controlling agent is uniformly dispersed in the above-mentioned polyethylene oxide, a controlled-release pharmaceutical composition containing this sized product, and a method of manufacturing a controlled-release pharmaceutical composition containing this sized product.

A controlled-release pharmaceutical composition with good uniformity of content can be presented by using powder particles of polyethylene oxide with powder properties suitable for tableting, which is obtained by uniform dispersion of the specific size controlling agent for polyethylene oxide of the present invention.

31 Claims, No Drawings

PHARMACEUTICAL COMPOSITION FOR CONTROLLED RELEASE OF ACTIVE SUBSTANCES AND MANUFACTURING METHOD THEREOF

CROSS-REFERENCE TO RELATED APPLICATIONS

The present application claims priority to U.S. Patent Application No. 60/453,046, filed Mar. 6, 2003, the disclosure of which is hereby incorporated by reference in its entirety for all purposes.

FIELD OF THE INVENTION

The present invention pertains to a pharmaceutical composition for controlled release, which comprises a drug, polyethylene oxide with a molecular weight of 2,000,000 or higher, and a specific size controlling agent for the above-mentioned polyethylene oxide and wherein the above-mentioned drug and above-mentioned specific size controlling agent are uniformly dispersed in the above-mentioned polyethylene oxide. Moreover, the present invention pertains to a method of manufacturing this controlled-release pharmaceutical composition as well as a controlled-release pharmaceutical preparation comprising particles of this controlled-release pharmaceutical composition.

BACKGROUND OF THE INVENTION

Sustained-release pharmaceutical preparations are developed for the purpose of improving compliance as a result of reducing the number of times they are administered or preventing adverse reaction by making the blood concentration fluctuations (peak/trough) smaller and thereby realizing stable therapeutic results, and various pharmaceutical preparations have been developed in recent years. Various sustained-release pharmaceutical preparations have been created by the present applicant as well. Of these, hydrogel sustained-release pharmaceutical preparations comprising a hydrophilic base (also gelation enhancer hereafter) and hydrogel-forming polymer can be easily manufactured because the composition and components are simple. This sustained-release pharmaceutical preparation can release a drug in the upper digestive tract, including the stomach and the small intestine, as well as the lower digestive tract, including the colon. In other words, the entire digestive tract can be used as the site of absorption. Therefore, it is highly practical and very useful as a pharmaceutical preparation with small inter-subject variation in terms of drug absorption in humans (for instance, refer to Patent Reference 1: International Publication Pamphlet No. 94/06414).

The inventors of inventions relating to the above-mentioned sustained-release pharmaceutical preparations proposed various polymers as hydrogel-forming polymers, but of these, polyethylene oxide is capable of imparting particularly good controlled-release performance to the pharmaceutical preparation and therefore, polyethylene oxide is usually selected as the polymer of first choice for the hydrogel-forming polymer. However, polyethylene oxide is a water-soluble thermoplastic resin in the form of a white powder or granules whose molecular weight reaches several 100,000 to several 1,000,000 that is obtained by polymerization of ethylene oxide, and polyethylene oxide with a molecular weight of 2,000,000 or higher becomes very sticky when exposed to moisture. Therefore, when water is added to polyethylene oxide or polyethylene oxide is handled under high humidity, it shows a very high viscosity, and polyethylene oxide can therefore be perceived as a substance that is difficult to handle during each process of pulverization, granulation, tableting, and the like, particularly during granulation. Therefore, methods have been presented in the past, including wet granulation, whereby for example, a chloride solvent such as dichloromethane or carbon tetrachloride or an alcohol solvent such as methanol, ethanol, or propanol is used alone or as a mixture with water direct tableting, and dry granulation when sustained-release pharmaceutical preparations that use polyethylene oxide, particularly matrix-type controlled-release pharmaceutical preparations that contain polyethylene oxide as the controlled-release base, contain a high concentration of polyethylene oxide with a high viscosity, (for instance, refer to Patent Reference 1: International Publication Pamphlet No. 94/06414, Patent Reference 2: International Publication Pamphlet No. 01/10466, Patent Reference 3: Specification of U.S. Pat. No. 5,273,758).

In addition, there is also a method of producing a pharmaceutical preparation by spray granulation of tablet starting materials comprising polyethylene oxide with a molecular weight of 100,000 using an aqueous hydroxypropylmethyl cellulose solution (Patent Reference 4: Specification of U.S. Pat. No. 4,662,880, Patent Reference 5: Specification of U.S. Pat. No. 4,810,502 (corresponds to Japanese Kokai Patent No. Hei 7-215869)). Although the conditions of wet granulation, and the like, are not entered to such an extent that granulation can be conducted by persons in the field, polyethylene oxide with a molecular weight of 2,000,000 or higher has a viscosity of 2,000 mPa·s or higher (millipascal second: aqueous 2% w/v solution, 25° C.) and this viscosity is dramatically higher than the viscosity of polyethylene oxide with a molecular weight of 100,000 of 30 to 50 mPa·s (aqueous 5% w/v solution, 25° C.). Therefore, it appears that when the same wet granulation method is used, granulation proceeds too far or a powder the particles of which become thread-like in appearance is produced and a powder that is appropriate for tableting cannot be made in that powder particles with poor fluidity are produced, and the like.

Furthermore, it goes without saying that when a controlled-release pharmaceutical preparation containing a low dose of drug is made, it must be made so that the active ingredient is contained uniformly per unit of the pharmaceutical preparation. Nevertheless, there are also problems with direct tableting and dry granulation in that the drug is scattered and the drug content is reduced, or uniformity of drug content is diminished, and further, productivity is poor because the granulation/pulverization process is repeated, and the like.

Furthermore, a variety of problems are indicated with wet granulation using an organic solvent, including environmental pollution, safety during manufacture (risk of explosion, and the like), expenditure on manufacturing facilities (explosion-proof equipment, use of organic solvents, and recovery facilities), and the like (for instance, refer to Patent Reference 3).

Patent Reference 1:
International Publication Pamphlet No. 94/06414
Patent Reference 2:
International Publication Pamphlet No. 01/10466
Patent Reference 3:
Specification of U.S. Pat. No. 5,273,758
Patent Reference 4:
Specification of U.S. Pat. No. 4,662,880
Patent Reference 5:
Specification of U.S. Pat. No. 4,810,502 (corresponds to Japanese Kokai Patent No. Hei 7[1995]-215869)

Consequently, there is the need today for the presentation of a powder that is appropriate for tableting in order to manufacture a pharmaceutical composition for controlled release of active substances containing polyethylene oxide with a molecular weight of 2,000,000 or higher and having good uniformity of drug content, the presentation of a controlled-release pharmaceutical composition containing this powder, and the presentation of a method of manufacturing this powder or a controlled-release pharmaceutical composition containing this powder.

DISCLOSURE OF THE INVENTION

The present inventors knew that many problems are encountered and realistically, manufacture is difficult during manufacturing a powder for controlled-release by aqueous system by using polyethylene oxide particles when the wet granulation method using a conventional binder is employed. That is, for instance, a powder that is appropriate for tableting cannot be manufactured because various diverse problems are encountered. For instance, when a binder that has binding force but shows poor plasticity, such as PVP, is used, granulation proceeds too far and powder particles with a high specific volume and poor fluidity are obtained, when a saccharide that has viscosity increasing power and binding force but becomes thread-like during spray drying, such as sorbitol, or a surfactant that has plasticity but shows poor binding force, such as polysorbate, is used, a powder with a small particle diameter is produced (the powder further breaks down into very fine particles) and becomes a powder that has a strong tendency toward being scattered and therefore, tableting is obstructed, and the like.

Therefore, the present inventors discovered that when a portion of the polyethylene glycol (also PEG hereafter) that is used as a gelation enhancer (hydrophilic base) of the components of the above-mentioned hydrogel-forming sustained release pharmaceutical preparation is added to a suspension of the drug and this suspension is sprayed on the polyethylene oxide, polyethylene oxide with a high viscosity does not become thread-like and can be sized into powder that has properties (specific volume, and the like) suitable for tableting. Surprisingly, the inventors discovered that even if a suspension containing a low dose of the drug is sprayed, the controlled-release pharmaceutical preparation consisting of this spray-dried product is a pharmaceutical preparation with superior uniformity of content.

As a result of further intense studies focusing on polyethylene oxide, the inventors discovered that when polyethylene oxide of a high viscosity and PEG in solid form are used for the fluidized bed granulator and an aqueous solution of the drug is sprayed on this, a polyethylene oxide sized product showing properties suitable for tableting can be produced, as with the above-mentioned method, and that superior uniformity of content is displayed by the controlled-release pharmaceutical preparation obtained by tableting this sized product.

Furthermore, the inventors also discovered that powder particles with polyethylene oxide properties that are appropriate for tableting, and a controlled-release pharmaceutical preparation with excellent uniformity of content that is obtained by tableting these polyethylene oxide powder particles are obtained when hydroxypropylmethyl cellulose (also RPMC hereafter), hydroxypropyl cellulose (also HPC hereafter) or methyl cellulose (also MC hereafter) of a specific viscosity grade is used as with PEG.

The details of this mechanism are still unclear. The polyethylene oxide product itself is a powder that is an aggregate of very fine particles and when water is used, this is broken down into fine particles, or on the other band, marked granulation will proceed. However, it is hypothesized that by selecting and using a specific substance with the appropriate plasticity and binding force, the polyethylene oxide particles themselves will rebind with the polyethylene oxide powder particles that have properties appropriate for tableting and thereby be sized. The polyethylene oxide powder of the present invention is also referred to hereafter as the polyethylene oxide sized product or simply the sized product.

The present invention is based on this series of discoveries, presenting 1. a pharmaceutical composition for controlled release comprising a sized product, which comprises (a) a drug, (b) polyethylene oxide with a viscosity-average molecular weight of 2,000,000 or more, and (c) a size controlling agent for (b) polyethylene oxide and wherein of said three components, at least size controlling agent (c) is uniformly dispersed in polyethylene oxide (b), 2. a pharmaceutical composition for controlled release according to above-mentioned 1, wherein (c) size controlling agent for (b) polyethylene oxide is one or two or more selected from the group consisting of polyethylene glycol that is solid at ordinary temperature, hydroxypropylmethyl cellulose of 2 to 15 mPa·s (2% w/v), hydroxypropylmethyl cellulose of 2 to 10 mPa·s (2% w/v), and methyl cellulose of 2 to 15 mPa·s (2% w/v), 3. a pharmaceutical composition for controlled release according to above-mentioned 1, wherein the amount of (c) size controlling agent for (b) polyethylene oxide is 0.5 to 60.wt % per polyethylene oxide (b), 4. a pharmaceutical composition for controlled release according to above-mentioned 1, wherein when polyethylene glycol is selected as (c) size controlling agent for (b) polyethylene oxide, the amount is 0.5 to 60 wt % per unit of the pharmaceutical preparation, 5. a pharmaceutical composition for controlled release according to above-mentioned 1, wherein the amount of polyethylene oxide (b) is 10 to 95 wt % per unit of the pharmaceutical preparation, 6. a pharmaceutical composition for controlled release according to above-mentioned 1, wherein the amount of polyethylene oxide (b) added is at least 70 mg per unit of the pharmaceutical preparation, 7. a pharmaceutical composition for controlled release according to above-mentioned 1, wherein viscosity-average molecular weight of polyethylene oxide (b) is 5,000,000 or higher, 8. a pharmaceutical composition for controlled release according to above-mentioned 1, which further comprises a hydrophilic base, 9. a pharmaceutical composition for controlled release according to above-mentioned 8, wherein the amount of water required to dissolve 1 g of the above-mentioned base is 5 ml or less (20±5° C.), 10. a pharmaceutical composition for controlled release according to above-mentioned 9, wherein the hydrophilic base is polyethylene glycol, sucrose, or polyvinyl pyrrolidone, 11. a pharmaceutical composition for controlled release according to above-mentioned 8, wherein the amount of hydrophilic base is 5 to 80 wt % per unit of the pharmaceutical preparation, 12. a pharmaceutical composition for controlled release according to above-mentioned 1 or 8, which further comprises yellow ferric oxide and/or red ferric oxide, 13. a pharmaceutical composition for controlled release according to above-mentioned 12, wherein the amount of yellow ferric oxide and/or ferric oxide is 0.3 to 20 wt % per polyethylene oxide, 14. a pharmaceutical composition for controlled release according to above-mentioned 1, wherein the amount of drug is 85 wt % or less per unit of the pharmaceuticalpreparation, 15. a pharmaceutical composition for controlled release according to above-mentioned 14, wherein the amount of drug is 10 wt % or less per unit of the pharmaceutical preparation, 16. a pharmaceutical composition for controlled release according to any one of above-mentioned 1 through 15, wherein the drug is tamsulosin hydrochloride, 17. a pharmaceutical composition for controlled release according to above-mentioned 1, which comprises essentially no organic solvent, and 18. a polyethylene oxide-containing powder for controlled-release pharmaceutical compositions, which contains polyethylene oxide (b) with a viscosity-average molecular weight of 2,000,000 or higher and (c) a size controlling agent for (b) polyethylene oxide and wherein at least size controlling agent (c) is uniformly dispersed in polyethylene oxide (b).

19. a sized product according to claim 18, wherein (c) a size controlling agent for (b) polyethylene oxide is one or two or more selected from the group consisting of polyethylene glycol that is solid at ordinary temperature, hydroxypropylmethyl cellulose of 2 to 15 mPa·s (2% w/v), hydroxypropylmethyl cellulose of 2 to 10 mPa·s (2% w/v), and methyl cellulose of 2 to 15 mPa·s (2% w/v), 20. a sized product according to claim 18, wherein the amount of (c) a size controlling agent for (b) polyethylene oxide is 0.5 to 60 wt % per polyethylene oxide (b), 21. a sized product according to claim 18, wherein when polyethylene glycol is selected as (c) a size controlling agent for (b) polyethylene oxide, the amount is 0.5 to 60 wt % per unit of the pharmaceutical preparation, 22. a sized product according to claim 18, wherein the amount of polyethylene oxide (b) is 10 to 95 wt % per unit of the pharmaceutical preparation, 23. a sized product according to claim 18, wherein the amount of polyethylene oxide (b) added is at least 70 mg per unit of the pharmaceutical preparation, 24. a sized product according to claim 18, wherein viscosity-average molecular weight of polyethylene oxide (b) is 5,000,000 or higher, 25. a sized product according to claim 18, which further comprises a hydrophilic base, 26. a sized product according to claim 25, wherein the amount of water required to dissolve 1 g of said base is 5 ml or less (20±5° C.), 27. a sized product according to claim 26, wherein the hydrophilic base is polyethylene glycol, sucrose, or polyvinyl pyrrolidone, 28. a sized product according to claim 25, wherein the amount of hydrophilic base is 5 to 80 wt % per unit of the pharmaceutical preparation, 29. a sized product according to any one of claims 18 to 25, which further comprises yellow ferric oxide and/or red ferric oxide, 30. a sized product according to claim 29, wherein the amount of yellow ferric oxide and/or ferric oxide is 0.3 to 20 wt % per polyethylene oxide, 31. a sized product according to claim 18, which further comprises a drug, 32. a sized product according to claim 18 or 31, wherein the amount of drug is 85 wt % or less per unit of the pharmaceutical preparation, 33. a sized product according to claim 32, wherein the amount of drug is 10 wt % or less per unit of the pharmaceutical preparation, 34. a sized product according to any one of claims 18 through 33, wherein the drug is tamsulosin hydrochloride, 35. a sized product according to claim 18, which comprises essentially no organic solvent, 36. a use of a sized product according to any one of claims 18 through 35 as a base for controlled-release preparation.

International Publication Pamphlet No. 92/10169 (corresponding to Japanese Patent No. 3239319) describes that the invention relating to a manufacturing method for a sustained-release dosage form for oral use, utilizing hydrophilic matrix gel component as a base, performing by using aqueous solution containing 20-50% solute, which is selected one or more from a poly-alcohol or polyvinylpyrrolidone, which is capable of becoming gel when administering orally to a mammal such as human, wherein gel-forming component is hydroxypropylmethylcellulose having various kinds of viscosity grade, wherein manufacturing wet-granules is preventing gelation of hydroxypropylmethylcellulose during granulation process. Said pamphlet also describes that wet-granulation by utilizing granulation in order to make granules obtained by granulation crushable as a granulation method for HPMC. However, the present invention is not a technology relating to method of wet-granulation, but discloses a method for re-sizing granulation by re-binding microscopic particles of polyethylenoxide which is broken up by spraying water, which becomes highly thread-like in appearance.

The "sizing" in the present Specification is different from the unit operation of "granulation" that is normally conducted by persons in this field, and it is also different from the process whereby a portion of a specific size is extracted by a sifting operation, and the like.

The "granulation" in the present Specification means a series of unit operations by which a granulated product of good uniformity is manufactured by binding particles to one another in order to improve adhesion and scattering of fine powder. In particular, when a pharmaceutical preparation with a low drug dose and good uniformity of content is to be manufactured, the drug is separately pulverized by itself, or pulverized after mixing with some of the additives to make fine particles in order to guarantee uniformity of content. Then a granulation process is generally conducted using a fluidized bed granulator. Consequently, growth of the particles is promoted by "granulation" and therefore, a powder with a large particle diameter and large specific volume ismanufactured.

In contrast to this, "sizing" is a series of unit procedures whereby water is sprayed onto the polyethylene oxide (Also PEO hereafter) powder with a high viscosity (commercial product) that is used in the present invention to manufacture powder particles (sized product) having a pre-determined particle diameter and a pre-determined specific volume. In detail, "polyethylene oxide sized products (Also PEO sized products hereafter)", for instance, in contrast to the case that part or all of particle breaks down into very fine particle when water is sprayed onto a PEO powder (commercial products) used in the present invention and become powder products being bound irregularly after drying, the case using the polyethylene oxide sizing agent used in the present invention, the PEO powder is sized to the powder particle which shows specific range of particle size and specific range of specific volume as a result of keeping the PEO powder from breaking down into very fine particles and/or as a result of re-binding into spherical shape during drying, and the like, are contained. That is, the "sizing" in the present specification means a series of single operations, not by which the PEO particles grow, but by which very fine particles of PEO that have been broken down by spraying with water re-bind during drying and re-form a powder of a size and specific volume appropriate for tableting.

The "particle diameter" in the present specification is represented by the average particle diameter defined as the cumulative 50% average particle diameter of the powder (μm) and the amount of fine powder (%) of 75 μm or smaller. Specific volume is represented by the volume per unit weight of the powder (ml/g).

"Comprises essentially no organic solvent" or "uses essentially no organic solvent" in the present specification means in addition to the fact that water only is always used as the solvent, organic solvent remains and/or is used within a range that is pharmaceutically acceptable, or organic solvent remains and/or is used within the range of environmental standards. To this extent, it does not exclude compositions that comprise organic solvent within a range that is pharmaceutically acceptable or within a range that does not exceed environmental standards.

The controlled-release pharmaceutical composition or the sized product of the present invention will now be described in detail:

There are no particular restrictions to the drug used in the present invention as long as it is an active ingredient that is effective in terms of treatment or in terms of prevention. Examples of this drug are anti-inflammatory, antipyretics, anticonvulsants, or analgesics such as indomethacin, diclofenac, diclotenac sodium, codeine, ibuprofen, phenylbutazone, oxyphenbutazone, mepyrizole, aspirin, etenzamide, acetaminophen, arninopyrine, phenacetin, butyl bromide scopolamine, morphine, ethomidrin, pentazocin, fenoprofen calcium, naproxen, celecoxib, valdecoxib, and tramadol, anti-rheumatic drugs such as etodolac, anti-tuberculosis drugs such as isoniazide, and ethambutol hydrochloride, drugs for treatment of circulatory disorders such as isosorbide nitrate, nitroglycerin, nifedipine, barnidepine hydrochloride, nicardipine hydrochloride, dipyridamol, amrinoine, indenolol hydrochloride, hydralazine hydrochloride, methyl dopa, furosemide, spironolactone, guanetidine nitrate, reserpine, amothrolol hydrochloride, lisinopril, methoprolol, pyrocarbine, and talsaltan, neuroleptics such as chloropromazine hydrochloride, amitripityline hydrochloride, nemonapride, haloperidol, moperon hydrochloride, perfenazine, diazepam, lorazopam, chlordiazepoxide, azinazolam, alprazolam, methylphenidate, milnasipran, peroxetin, risperidone, and sodium valproate, antiemetics such as metoclopramide, ramosetron hydrochloride, granisetron hydrochloride, ondansetron hydrochloride, and azasetron hydrochloride, antihistamines such as chlorpheniramine maleate and dipbenhydramine hydrochloride, vitamins such as thiamine nitrate, tocopherol acetate, cycothiarine, pyridoxal phosphate, cobamamide, ascorbic acid, and nicotinamide, drugs for gout such as allopurinol, colchicine, and probenecid, drugs for Parkinson's disease such as levodopa and selegiline, hypnotic sedatives such as amobatbitol, brornovaleryl urea, midazolam, and chloral hydrate, anti-malignant tumor drugs such as fluorouracil, carmnofur, acralvidine hydrochloride, cyclophosphamide, and thiodepa, anti-allergy drugs such as pseudoephedrin and terfenadine, drugs used to treat decongestant such as phenylpropanolamine and ephedrines, drugs used for diabetes such as acetohexamide, insulin, torbutarnide, desmopressin, and glypizine, diuretics such as hydrochlorothi- azide, polythiazide, and triamuteren, bronchodilators such as axrnophylline, formnoterol furmate, and theophylline, antitussives such as codeine phosphate, noscapine, dimernorphan phosphate, and dextromethorphan, anti-arrhythmia drugs such as quinidine nitrate, digitoxin, propapbenone hydrochloride, and procainamide, topical anesthetics such as ethyl aminobenzoate, lidocaine, and dibucaine hydrochloride, antiepilepsy drugs such as phenytoin, ethosuximide, and primidone, synthetic corticosteroids such as hydrocortisone, prednisolone, triamcinolone, and betamethazone, drugs for the digestive tract such as famotidine, ranitidine hydrochloride, cimetidine, sucralfate, sulpiride, tepreson, pravatol, 5-aminosalicylic acid, sulfathalazin, omeprazol, and lansoprazole, drugs for the central nervous system such as indeloxazine, idepenon, thiaprid hydrochloride, bipheuaelan hydrochloride, and calcium homopantotheoate, drugs for treatment of hyperlipidemia such as pravastatin sodium, simnvastatin, lovastatin, and atorvastatin, antibiotics such as ampicillin hydrochloride phthalidyl, cefotetan, and josamycin, BPH drugs such as tainsulosin, doxazosin mesylate, and terazosin hydrochloride, anti-asthma drugs such as pranlukast, zafirlukast, albuterol, ambroxol, budesonide, and reperbutenol, drugs used to improve peripheral circulation of prostaglandin I derivatives such as beraprost sodium, anticoagulants, hypotensive drugs, drugs used to treat heart failure, drugs used to treat the various complications of diabetes, drugs used to treat gastric ulcers, drugs used to treat skin ulcers, drugs used to treat hyperlipidemia, anti-asthma drugs, and the like. The drug can be used in free form or as a salt that is pharmaceutically acceptable. Moreover, one or a combination of two or more drugs can be used. Furthermore, even better results are obtained from the present invention when a very small amount of active ingredient that is effective in terms of treatment or prevention or a drug that is effective in low doses and is slightly water soluble is used as the drug in the present invention. Of the above-mentioned drugs, tamsulosin is particularly preferred as the drug.

The chemical name for tamsulosin is (R)(-)-5-[2-[[2-(o-ethoxyphenoxy)ethyl]amino]propyl]-2-methoxybenzene-sulfonamide and it is represented by the following structural formula. It was first disclosed together with its pharmaceutically acceptable salts in Japanese Kokai Patent No. Sho 56(1981)-110665.

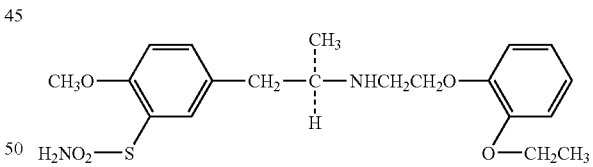

It is known that tamsulosin and its salts have adrenalin $\alpha_{1A}$ receptor-blocking activity, in other words, the same hydrochloride (tamsulosin hydrochloride) has the ability to block the $\alpha_1$ receptor of the urethra and prostate and therefore is a popular drug for reducing pressure applied to the prostate along the pressure curvature inside the urethra and for improvement of the dysuria that accompanies prostatomegaly. Tamsulosin hydrochloride is also a drug that is clinically very useful in that it has been recognized as clinically effective for the treatment of lower urinary tract disorders.

Tamsulosin and its pharmaceutically acceptable salts can be easily procured by the manufacturing method entered in Japanese Kokai Patents No. Sho 56-110665 and No. Sho 62-114952, or by manufacturing in accordance with this method.

Tamsulosin can form a pharmaceutically acceptable acid or a base addition salt with a wide variety of inorganic and organic salts and bases. Such salts are also a part of the present invention. Examples of salts of inorganic acids, such as hydrochloric acid, sulfuric acid, and phosphoric acid, salts of organic acids, such as fumaric acid, malic acid, citric acid, and succinic acid, salts of alkali metals, such as sodium and potassium, and salts of alkali earth metals, such as calcium and magnesium. Hydrochlorides are most preferred in the present invention and these salts can be manufactured by conventional methods.

The amount of drug that is added is usually selected as needed and used as needed based on the type of drug and medical use (indications), and there are no special restrictions as long as it is the amount that is effective in terms of treatment or prevention. A drug that is effective in very small doses (low-dose drug) is particularly preferred because the desired effects of the present invention are even better. However, it can be easily assumed that uniformity of content can even be accomplished with drugs that are effective in high doses (high-dose drugs), and therefore, there are no particular restrictions to the amount of drug that is added. This amount that is added is illustrated later using a hydrogel sustained-release pharmaceutical preparation. However, it is preferably 85 wt % or less, more preferably. 80 wt % or less, further preferably 50 wt %, and more further preferably 10 wt % or less, of the total pharmaceutical preparation. It is 1 wt % or less when the drug is tamsulosin. The dose of tamsulosin or its pharmaceutically acceptable salt is determined as needed in accordance with the individual case taking into consideration the route of administration, the symptoms of the illness, the age and sex of the administration subject, and the like. The dose of tamsulosin hydrochloride is normally approximately 0.1 mg to 1.6 mg/day of active ingredient to one adult by oral administration and this is administered orally once a day.

There are no special restrictions to the polyethylene oxide (Also PEO hereafter) that is used in the present invention as long as it is one with which release of drug from the controlled-release pharmaceutical preparation containing PEO as the sustained release base can be controlled. Examples of this PEO are POLYOX® WSR-303 (viscosity-average molecular weight of 7,000,000, viscosity of 7,500 to 10,000 mPa·s (millipascal second: in an aqueous 1% W/V solution at 25° C.), POLYOX® WSR Coagulant (viscosity-average molecular weight of 5,000,000, viscosity of 5,500 to 7,500 mPa·s (in an aqueous1% W/V solution at 25° C.)), POLYOX® WSR-301 (viscosity-average molecular weight of 4,000,000, viscosity of 1,650 to 5,500 mPa·s (in an aqueous 1% W/V solution at25° C.)), and POLYOX® WSR N-60K (viscosity-average molecular weight of 2,000,000, viscosity of 2,000 to 4,000 mPa·s (in an aqueous 2% W/V solution at 25° C.) (all manufactured by The Dow Chemical Company), ALKOX® E-75 (viscosity-average molecular weight of 2,000,000 to 2,500,000, viscosity of 40 to 70 mPa·s (in an aqueous 0.5% W/V solution at 25° C.)), ALKOX® E-100 (viscosity-average molecular weight of 2,500,000 to 3,000,000, viscosity of 90 to 110 mPa·s (in an aqueous 0.5% W/V solution at 25° C.)), ALKOX® E-130 (viscosity-average molecular weight of 3,000,000 to 3,500,000, viscosity of 130 to 140 mPa·s (in an aqueous 0.5% W/V solution at 25° C.)), ALKOX® E-160 (viscosity-average molecular weight of 3,600,000 to 4,000,000, viscosity of 150 to 160 mPa·s (in an aqueous 0.5% W/V solution at 25° C.)), and ALKOX® E-240 (viscosity-average molecular weight of 4,000,000 to 5,000,000, viscosity of 200 to 240 mPa·s (in an aqueous 0.5% W/V solution at 25° C.) (all manufactured by Meisei Chemical Works, Ltd.), and PEO-8 (viscosity-average molecular weight of 1,700,000 to 2,200,000, viscosity of 20 to 70 mPa·s (in an aqueous 0.5% W/V solution at 25° C.)), PEO-15 viscosity-average molecular weight of 3,300,000 to 3,800,000, viscosity of 130 to 250 mPa·s (in an aqueous 0.5% W/V solution at 25° C.)), and PEO-18 (viscosity-average molecular weight of 4,300,000 to 4,800,000, viscosity of 250 to 480 mPa·s (in an aqueous 0.5% W/V solution at 25° C.)) (all manufactured by Sumitomo Seika Chemicals Co., Ltd.). Of these, PEO with a high viscosity at the time of gelling or with a high viscosity-average molecular weight is preferred. PEO with a viscosity of 2,000 mPa·s or higher in an aqueous 2% solution (25° C.) or with a viscosity-average molecular weight of 2,000,000 to 10,000,000. is preferred. PEO with a viscosity-average molecular weight of 4,000,000 to 10,000,000 is further preferred and that with a viscosity-average molecular weight of 5,000,000 to 10,000,000.is more further preferred. PEO with a viscosity-average molecular weight of 7,000,000 (for instance, POLYOX® WSR-303) is optimal. One or a combination of two or more PEO of different molecular weights, grades, and the like can be used.

There are no special restrictions to the amount of polyethylene oxide added as long as it is the amount with which release of the drug from the hydrogel-forming sustained-release pharmaceutical preparation can usually be controlled. However, it is preferred that it be 10 to 95 wt % per the total pharmaceutical preparation, and 15 to 90 wt % per the total pharmaceutical preparation is further preferred. Moreover, the amount of PEO that is added is preferably 70 mg or more, further preferably 100 mg or more, more further preferably 150 mg or more, per 1 unit of the pharmaceutical preparation. If the drug is tamsulosin hydrochloride, the amount of PEO added is preferably 100 mg to 300 mg, further preferably 150 mg to 250 mg, more further preferably 200 mg. A controlled-release pharmaceutical preparation (tablet) that is manufactured using this amount of PEO with a viscosity-average molecular weight of 7,000,000 (for instance, PEO with the brand name POLYOX® WSR-303) from among the above-mentioned type sof PEO will provide marked effects as a controlled-release pharmaceutical preparation.

There are no special restrictions to the size controlling agent for polyethylene oxide that is used in the present invention as long as it is powder particles that are suitable for tableting PEO of a high viscosity with an aqueous system. This size controlling agent is a substance having the appropriate plasticity and binding ability. Solid polyethylene glycol (PEG hereafter), low viscosity grades of hydroxypropylmethyl cellulose (HPMC hereafter), hydroxypropyl cellulose (HPC hereafter), and methyl cellulose (MC hereafter), and the like are given as this size controlling agent. This size controlling agent can be used dissolved and/or suspended in water. Moreover, because the above-mentioned effects can be realized with PEG by dissolving part of the PEG in solid form with high water solubility using sprayed water, it can be used as the PEO size controlling agent of the present invention, even if it is added in solid form.

PEG that is solid at ordinary temperature (PEG4000, PEG6000, PEG8000) is preferred as the PEG. Macrogol 4000 (Japanese Pharmacopoiea, molecular weight of 2,600 to 3,800, brand name: Macrogol 4000/Sanyo Chemical Industries, Ltd., NOF Corporation, Lion Corporation, and the like), Macrogol 6000 (Japan Pharmaceopoiea, molecular weight of 7,300 to 9,300, brand name: Macrogol 6000/Sanyo Chemical Industries, Ltd., NOF Corporation, Lion Corporation, and the like), Macrogol 20000 (Japan Pharmacopoeia, molecular weight of 15,000 to 25,000, brand name: Macrogol 20000 (Sanyo Chemical Industries, Ltd., NOF Corporation, Lion Corporation, and the like), polyethylene glycol 8000 (USP/

NF, molecular weight of 7,000 to 9,000, brand name: Polyethylene glycol 8000/The Dow Chemical Company, and the like), and the like are specifically given. Low-viscosity grades of HPCM (viscosity of 2 to 15 mPa·s, aqueous 2% W/V solution, 20° C.) are preferred. The brand names of TC-5E (viscosity of 3 mPa·s, aqueous 2% W/V solution, 20° C., Shin-Etsu Chemical Co., Ltd.), TC-5R (viscosity of 6 mPa·s, aqueous 2% W/V solution, 20° C., Shin-Etsu Chemical Co., Ltd.), TC-5S (viscosity of 15 mPa·s, aqueous 2% W/V solution, 20° C., Shin-Etsu Chemical Co., Ltd.), Methocel E3 (viscosity of 3 mPa·s, aqueous 2% W/V solution, 20° C., The Dow Chemical Company), Methocel E5 (viscosity of 5 mPa·s, aqueous 2% W/V solution, 20° C., The Dow Chemical Company), Methocel E15 (viscosity of 15 mPa·s, aqueous 2% W/V solution, 20° C., The Dow Chemical Company), and the like are specifically given. Low viscosity grades (viscosity of 2 to 10 mPa·s, aqueous 2% W/V solution, 20° C.) are preferred as the HPC. The brand names of HPC-SSL (viscosity of 3.0 to 5.9 mPa·s, aqueous 2% W/V solution, 20° C., Nippon Soda Co., Ltd.), IMC-SL (viscosity of 2.0 to 2.9 mPa·s, aqueous 2% W/V solutoin, 20° C., Nippon Soda Co., Ltd.), HPC-L (viscosity of 6.0 to 10.0 mPa·s, aqueous 2% W/V solution, 20° C., Nippon Soda Co., Ltd.), and the like are specifically given. Low viscosity grades (viscosity of 2 to 15 mPa·s, aqueous 2% W/V solution, 20° C.) are preferred as the MC. The brand name of Methocel A15-LV (viscosity of 15 mPa·s, aqueous 2% W/V solution, 20° C., The Dow Chemical Company), Metolose SM4 (viscosity of 4 mPa·s, aqueous 2% W/V solution, 20° C., Shin-Etsu Chemical Co., Ltd.), Metolose SM15 (viscosity of 15 mPa·s, aqueous 2% W/V soluition, 20° C., Shin-Etsu Chemical Co., Ltd.), and the like are specifically given.

PEG and/or HPMC are further preferred as the size controlling agent for polyethylene oxide, and PEG is the ideal size controlling agent of the present invention, even if added in powder form. One or a combination of two or more size controlling agents of the present invention can be used. The method whereby water or an aqueous solution containing a binder is sprayed after physical mixing, the method whereby an aqueous solution containing a size controlling agent is sprayed, and the like are given as the state in which the size controlling agent is used.

There are no special restrictions to the amount of size controlling agent for polyethylene oxide that is used as long as it is the amount that can size PEO with an aqueous system. It is usually 0.5 to 60 wt % per unit of pharmaceutical preparation. When PEG as the size controlling agent of the present invention is sprayed in the form of an aqueous solution, the amount is preferably 0.5 to 3 wt %, further preferably 1 to 2 wt %, per unit of pharmaceutical preparation. When a substance other than PEG as the size controlling agent of the present invention is sprayed in the form of an aqueous solution, the amount is preferably 0.5 to 3 wt %, further preferably 1 to 2 wt %, per unit of pharmaceutical preparation. Moreover, when PEG is used as a solid size controlling agent, the amount is preferably 5 to 60 wt %, further preferably 10 to 30 wt %.

The amount of substance other than PEG as the size controlling agent that is used in the form of an aqueous solution is small when compared to the amount that is usually used as a binder (3 to 5 wt %). If less than 0.5 wt % is used, there will be problems in that the desired sizing will not be performed and there will be a large amount of fine powder, there will be a reduction in uniformity of drug content, a powder of poor fluidity will further be produced, and the like. If the amount is more than 3 wt %, granulation will proceed to too great an extent and as a result, fluidity of the powder will decrease, the powder will be too large, re-pulverizing after drying will be necessary, and the like and as a result, there is concern that problems will remain with uniformity of drug content.

There are no special restrictions to the controlled-release pharmaceutical composition of the present invention as long as it is a pharmaceutical composition, particularly a pharmaceutical preparation, with which release of the drug is controlled. The hydrogel sustained-release pharmaceutical preparation in International Publication Pamphlet No. 94/06414 is an example of this controlled-release pharmaceutical composition (particularly a controlled-release pharmaceutical preparation). The above-mentioned hydrogel sustained-release pharmaceutical preparation consists of a drug, a gelation enhancer with a specific solubility (hydrophilic base), and PEO of a specific molecular weight as the basic structural components. Moreover, when PEO is used as the controlled-release pharmaceutical preparation, yellow ferric oxide and/or red ferric oxide are added as PEO stabilizers, as entered in International Publication Pamphlet No. 01/10466. The mechanism of drug release is as entered in International Publication Pamphlet No. 94/06414 with any pharmaceutical preparation. That is, the controlled-release pharmaceutical preparation absorbs water during its stay in the upper digestive tract to undergo substantially complete gelation (70% or higher, preferably 80% or higher) and then it moves to the lower digestive tract as the surface of the pharmaceutical preparation is eroded and drug continues to be released with erosion. Therefore, good and continuous release and absorption of the drug are performed, even in the colon with a small water content. The controlled-release pharmaceutical composition or hydrogel sustained-release pharmaceutical preparation can also contain pharmaceutical fillers as needed.

When the controlled-release pharmaceutical preparation of the present invention further contains a hydrophilic base, there are no special restrictions to the hydrophilic base (gelation enhancer) required in the present invention as long as it can be dissolved before the PEO that is required in the present invention gels. The amount of water needed to dissolve 1 g of this hydrophilic base is preferably 5 ml or less (20±5° C.), further preferably 4 ml or less (same temperature). Hydrophilic polymers such as polyethylene glycol (for instance, Macrogol 400, Macrogol 1500, Macrogol 4000, Macrogol 6000, and Macrogol 20000 (all manufactured by NOF Corporation)) and polyvinyl pyrrolidone (for instance, PVP® K30 (BASF)), sugar alcohols such as D-sorbitol and xylitol, saccharides such as sucrose, maltose, lactulose, D-fructose, dextran (for instance, Dextran 40), and glucose, surfactants such as polyoxyethylene-hydrogenated castor oil (for instance, Cremophor® RH140 (BASF), HCO40, HCO-60 (Nikko Chemicals), polyoxyethylene polyoxypropylene glycol (for instance, Pluronic® F68 (Asahi Denka Co., Ltd.) and polyoxyethylene sorbitan higher fatty acid esters (for instance, Tween 80 (Kanto Kagaku Co., Ltd.), salts such as sodium chloride and magnesium chloride, organic acids such as citric acid and tartaric acid, amino acids such as glycine, β-alanine, and lysine hydrochloride, and aminosaccharides such as meglumine are given as examples of the hydrophilic base. Polyethylene glycol, sucrose, and polyvinyl pyrrolidone are preferred and polyethylene glycol (particularly Macrogol 6000 and Macrogol 8000) are further preferred. One or a combination of two or more hydrophilic bases can be used in the present invention.

The amount of hydrophilic base (gelation enhancer) that is used is preferably 5 to 80 wt % per total pharmaceutical preparation, further preferably 5 to 60 wt % per total pharmaceutical preparation. Furthermore, when the gelation enhancer serves as what is called a size controlling agent in the present invention, the amount of gelation enhancer is calculated as the combined amount.

It is preferred that yellow ferric oxide and/or red ferric oxide is added as the PEO stabilizer to the controlled-release pharmaceutical preparation of the present invention (U.S. Pat. No. 9,629,405 (refer to corresponding International Patent Publication Pamphlet No. 01/10466)). The amount of this stabilizer is preferably 1 to 20 wt %, further preferably 3 to 15 wt %, per total mount of pharmaceutical preparation when it is a physical mixture in a matrix. For instance, the amount of red ferric oxide is preferably 5 to 20 wt %, further preferably 10 to 15 wt %, per total amount of pharmaceutical preparation. The amount of yellow ferric oxide is preferably 1 to 20 wt %, further preferably 3 to 10 wt %. When added with a film coating, the amount is preferably 0.3 to 2%, further preferably 0.5 to 1.5%, per tablet weight. The concentration of yellow ferric oxide or red ferric oxide that is present in the film in this case is preferably 5 to 50%, further preferably 10 to 20%. The "physical mixture in a matrix" used here is defined as a means with which, for instance, drug, polyethylene oxide and the above-mentioned ferric oxide are uniformly dispersed so that the drug and the above-mentioned ferric oxide are uniformly dispersed in the PEO that becomes the main base of the controlled-release pharmaceutical preparation. Moreover, the "film coating" here is defined as for instance, dissolution or suspension of the above-mentioned ferric oxide in a water-soluble polymer solution such as hydroxypropyl methyl cellulose and coating tablets that have been separately prepared with this in the form of a thin film. The yellow ferric oxide and/or red ferric oxide of the present Invention can usually be found anywhere in the pharmaceutical preparation. For instance, the yellow ferric oxide and/or red ferric oxide can be present in the film of film coating, in the granulation product of granulation, or in the matrix (for instance, near the polyethylene oxide).

A variety of pharmaceutical fillers are further used as needed with the controlled-release pharmaceutical composition of the present invention to make a pharmaceutical preparation here are no special restrictions to these drug fillers as long as they are pharmaceutically and pharmacologically acceptable. For instance, binders, disintegrating agents, sour flavorings, foaming agents, artificial sweeteners, fragrances, lubricants, coloring agents, stabilizers, buffer agents, and antioxidants are used. Hydroxypropylmethyl cellulose, hydroxypropyl cellulose, polyvinyl alcohol, methyl cellulose, hydroxypropyl cellulose, polyvinyl alcohol, methyl cellulose, and gum arabic are examples of binders. Corn starch, starches, carmellose calciuma, carmellose sodium, and hydroxypropyl cellulose with a low degree of substitution are examples of the disintegrating agent. Citric acid, tartaric acid, and malic acid are examples of the sour flavoring. Sodium bicarbonate is an example of the foaming agent. Saccharin sodium, dispotassium glycyribizinate, aspartamne, stevia, and sornatin are examples of artificial sweeteners. Lemon, lemon lime, orange, and menthol are examples of fragrances. Magnesium stearate, calcium stearate, sucrose fatty acid ester, polyethylene glycol, talc, and stearic acid are examples of lubricants. Yellow ferric oxide, red ferric oxide, yellow food colorings No. 4 and No. 5, red food colorings No. 3 and No. 102, and blue food coloring No. 3 are examples of coloring agents It is confirmed that yellow ferric oxide and red ferric oxide have a particularly marked photostabilizing effect on tamsulosin hydrochloride when used in controlled-release pharmaceutical preparations to which tamsulosin hydrochloride have been added, and these coloring agents are also given as photostabilizers. The amount of coloring agent is usually a trace (a trace to 0.1 wt %). However, when added as the stabilizer, there are no special restrictions to the amount as long as it usually provides stabilizing effects as a photo-stabilizer, but it is normally 0.1 to 2 wt %, preferably 0.5 to 1 wt %. Citric acid, succinic acid, fumaric acid, tartaric acid, ascorbic acid and their salts, glutamic acid, glutamine, glycine, aspartic acid, alanine, arginine, and their salts, magnesium oxide, zinc oxide, magnesium hydroxide, phosphoric acid, boric acid and their salts, and the like are given as buffer agents. Ascorbic acid, dibutyl hydroxytolueme and propyl gallate are given as examples of antioxidants. Appropriate amounts of one or a combinate of two or more pharmaceutical fillers can be added as needed.

The method of manufacturing the controlled-release pharmaceutical composition or the sized product of the present invention will now be described in detail:

The processes involved in the manufacture of the controlled-release pharmaceutical composition of the present invention are essentially as follow:

(1) Process of pulverization and mixing of components, (2) Process of suspending and/or dissolving PEO size controlling agent (process of preparation of size controlling agent solution)

(3) Process of sizing and drying whereby the size controlling agent solution that was prepared in above-mentioned process (2) is sprayed onto PEO of a high viscosity with a molecular weight of 2,000,000 or higher (process of preparing PEO sizing product (powder particles)

(4) Process of uniformly mixing PEO sizing product obtained by above-mentioned process (3) and a pharmaceutically acceptable filler (5) Process of molding (1) Process of Pulverization and Mixing of Components There are no special restrictions to the equipment and means of this process as long as it is a method whereby usually pulverization is pharmaceutically possible. There are no special restrictions to the equipment or means of the process of mixing of each component that follows pulverization as long as it is a method by which usually each component can be uniformly mixed pharmaceutically.

A hammer mill, ball mill, jet pulverization device, and colloid mill are examples of the pulverization device. There are no special restrictions to the pulverization conditions as long as they are selected as needed. For instance, in the case of the hammer mill, punch diameter of the screen is usually 0.5 to 5 mm, preferably 0.8 to 2 mm. The powder feed speed is usually 50 to 500 g/minute, preferably 100 to 200 g/minute. A V-type mixer, ribbon mixer, container mixer, and high-shear agitating mixer are examples of the mixing device. There are no special restrictions to the mixing conditions as long as they are selected as needed. For instance, in the case of a container mixer with a capacity of 20 L, the rotating speed is usually 10 to 40 rpm, preferably 20 to 30 rpm. It is preferred that each component is pre-mixed using a sieve of, for instance, 42 mesh (opening of 355 μm) for pulverization pre-treatment of each component.

(2) Process of Suspending and/or Dissolving the PEO Size Controlling Agent (Process of Preparation of Size Controlling Agent Solution)

There are no particular restrictions to the equipment or means of this process as long as it is a method whereby the size controlling agent can be uniformly dissolvedand/or suspended.

The magnetic stirrer and propeller mixer are examples of the suspending (dissolving) device. There are no special restrictions to the conditions for preparing the size controlling agent solution as long as they are selected as needed. There are no special restrictions to the concentration of the size controlling agent solution as long as it is the concentration of size controlling agent that is sprayed by fluidized bed granulation. This concentration is usually 1 to 50% W/W, preferably 2 to 30% W/W. With PEG it is 1 to 50% W/W, preferably 5 to 30% W/W. With HPMC, it is 1 to 20% W/W, preferably 2 to 10% W/W. With HPC it is 1 to 20% W/W, preferably 2 to 10% W/W. With MC it is 1 to 20% W/W, preferably 2 to 10% W/W.

(3) Process of Sizing and Drying Whereby the Size Controlling Agent Solution that was Prepared in Above-mentioned Process (2) is Sprayed onto PEO of a High Viscosity with a Molecular Weight of 2,000,000 or Higher (Process of Preparing PEO Sized Product (Powder Particles)

There are no special restrictions to the equipment or means of this process as long as it is a method by which PEO with a high viscosity can be wet sized using an aqueous solution of a PEO size controlling agent.

Examples of the spraying device (method) are the high-shear agitation granulation method, crushing (pulverization) granulation method, fluidized bed granulation method, extrusion granulation method, tumbling granulation method, and spray granulation method, or device for by using its method thereof. The fluidized bed granulation method or device is preferred and the tumbling fluidized bed granulation or device is particularly preferred because it is possible to easily and uniformly mix a low-dose drug and hydrophilic base with PEO of a high viscosity.

Examples of the sizing device are the fluidized bed granulator (for instance, the flow coater, Freund Industry Co., Ltd., the GPCG, Glatt Co., Ltd.), a granulation and coating device equipped with a horizontal rotating disc having a flat powder contact part (for instance, a centrifugal fluidization and granulator (for instance, the CF granulator of Freund Industry Co., Ltd.), and a granulation and coating device having an aeration part and wherein a rotating disk with a flat surface is placed at the bottom of the fluidized bed (for instance, the spiral flow or flow coater with rotor container, both made by Freund Industry Co., Ltd.).

There are no special restrictions to the amount of water during sizing as long as it is the amount with which size controlling agent (and preferably drug) can be uniformly dissolved and/or suspended (dispersed). When PEG is used in solid form, there are no special restrictions as long as it is the amount that can size the PEO.

When used in liquid form, it is usually 10 wt % or less, preferably 8 wt % or less, further preferably 5 wt % or less, per PEO. There are no special restrictions to the method of adding water during sizing as long as it is a method by which a nonuniform product consisting of mass of powder aggregate and untreated powder is not usually produced. Examples are the continuous spraying method whereby water is continuously added and the intermittent spraying method whereby a drying process and further, a shaking process are set up somewhere in the granulation process.

There are no special restrictions to the speed with which water is added during granulation as long as it is a speed with which a nonuniform product consisting of masses of powder aggregate and untreated powder is not usually produced. For instance, it is usually 0.1 to 1 wt %/min, preferably 0.2 to 0.8 wt %/min, further preferably 0.4 to 0.6 wt %/min, per PEO in the case of fluidized bed granulation.

There are no special restrictions to the temperature of the powder during sizing as long as it is a temperature that will not induce thermal denaturation of the PEO. For instance, it is 20° C. to the melting point of PEO (62 to 67° C.), preferably 20° C. to 50° C., further preferably 20° C. to 35° C., ideally 25° C. to 30° C.

There are no special restrictions to the equipment and means of the drying process as long as it is a method whereby the sized product is dried. Examples of the drying device are the fluidized bed granulator (for instance, the flow coater, Freund Industry Co., Ltd., the GPCG, Glatt Co., Ltd.), a granulation and coating device equipped with a horizontal rotating disc having a flat powder contact part (for instance, a centrifugal fluidization and granulator (for instance, the CF granulator of Freund Industry Co., Ltd.), and a granulation and coating device having an aeration part and wherein a rotating disk with a flat surface is placed at the bottom of the fluidized bed (for instance, the spiral flow or flow coater with rotor container, both made by Freund Industry Co., Ltd.). There are no special restrictions to the drying conditions as long as they are conditions under which a sized article will usually dry in the fluidized bed. For instance, when drying inlet temperature is set at 50° and drying is performed until the sized article temperature becomes 40° C., drying of the sized article is almost complete. The aeration drying method and reduced pressure drying method can also be used as the drying method.

The powder particles (sized product) that are obtained can be evaluated by the following methods:

[Average Particle Diameter]

The "average particle diameter" means the cumulative 50% average particle diameter. The average particle diameter can be determined with an automatic particle diameter distribution determination device (brand name: Robot Sifter, Seishin Enterprise Co., Ltd.), and the like. Usually it is approximately 50 to 500 μm, preferably approximately 60 to 300 μm, further preferably 80 to 200 μm.

[Amount of Very Fine Powder]

The "amount of very fine powder" means the amount of particles that are 75 μm or smaller. Particle size can be determined with an automatic particle diameter distribution determination device (brand name: Robot Sifter, Seishin Enterprise Co., Ltd.), and the like. As an evaluation criterion, the amount of particles that are 75 μm or smaller is preferably 20% or less, further preferably 15% or less.

[Specific Volume]

Using a powder property determination device (Powder Tester PT-D, Hosokawa Micron Corporation), a specific amount of sample is placed on a 20 mesh sieve and continuously allowed to fall naturally through a funnel into a receptacle with an inner capacity of 100 ml while being vibrated. After the pile of sample is scraped off of the receptacle with a flat metal plate, the mass of the receptacle into which the sample has been introduced is weighed and specific volume is calculated. It is preferably 1.5 to 3.5 mL/g, further preferably 2.0 to 3.0 mL/g.

[Angle of Repose]

Using a powder property determination device (Powder Tester PT-D, Hosokawa Micron Corporation), the "angle of repose" is found by allowing a specific amount of sample to continuously fall onto a disc-shaped determination table as it is vibrated until the sample begins to spill from the edge of the table, forming a cone-shaped pile, and reading the angle of inclination of this pile with a protractor. As an evaluation criterion, the angle of repose is preferably 45° or smaller, further preferably 42° or smaller.

[Fluidity] (Degree of Compression)

Using a powder property determination device (Powder Tester PT-D, Hosokawa Micron Corporation), a specific amount of sample is placed on a 20 mesh sieve and continuously allowed to fall naturally through a funnel into a receptacle with an inner capacity of 100 ml while being vibrated. After the pile of sample is scraped off of the receptacle with a flat metal plate, the mass of the receptacle into which the sample has been introduced is weighed and minimum apparent density is calculated. A top vessel is further attached and excess powder is added and tapped with a vibrator. The topvessel isremoved and the pile of sample is scraped off of the receptacle with a flat metal plate. Then the mass of the receptacle into which the sample has been introduced is weighed and tapped apparent density is determined. The degree of compression of the powder is calculated from the minimum density and the tapped density using the following formula. It is preferably 15% or less, further preferably 10% or less.

Degree of compression (%)=(*T*–*M*)/*T*×100

T: Tapped density
M: Minimum density (4) Process of Uniformly Mixing PEO Sizing Product Obtained by Above-mentioned Process (3) and a Pharmaceutically Acceptable Filler There are no special restrictions to the equipment or means of this process as long as it is a method whereby the PEO sized product obtained by above-mentioned process (3) and pharmaceutically acceptable filler are uniformly mixed. The method whereby they are uniformly mixed in one or two processes selected from the group consisting of (1) the process of dissolving and/or suspending in the spraying liquid, (2) the process whereby the powder particles are prepared, and (3) the process of being uniformly mixed with a pharmaceutically acceptable filler is an example.

(5) Process of Molding

There are no special restrictions to the equipment or means of this process as long as it is a method with which a pharmaceutical compression molded article (preferably tablets) is usually made.

Examples of the tableting device are rotary tablet machine (for instance HT P-22, Hata Iron Works, Ltd.) and a single tablet machine (for instance, KM-2, Okada Seiko Co., Ltd.). Examples of the tableting conditions are 20 to 30 rpm as the number of rotations of the turn table and a tableting pressure of 200 to 600 kgf/punch.

The sized product itself, or tablets, fine particles, granules, capsules of sized product packed in, for instance, gelatin hard capsules, that are made by conventional methods, and the like are given as the pharmaceutical composition (pharmaceutical preparation). There are no special restrictions to the method of manufacturing the controlled-release pharmaceutical composition of the present invention or its pharmaceutical preparation as long as it is a method whereby the desired pharmaceutical preparation is manufactured using combinations of the above-mentioned methods or conventional methods as needed.

PREFERRED EMBODIMENTS OF THE INVENTION

The present invention will now be explained in further detail with comparative examples, examples, and experiments, but this does. Dot mean that the present invention is limited to these examples and experiments.

Furthermore, although the examples of the present invention include an example in which the composition does not comprise a drug, this example is one where a very small dose of drug is used in the pharmaceutical preparation of the present invention, that is, a trace of drug (a trace dose that is effective in terms of treating or preventing disease) that is so small that it will not affect the properties of the PEO sized product is used in the pharmaceutical preparation of the present invention.

EXAMPLE 1

Four parts of Macrogol 6000 were dissolved in 36 parts of water while being mixed with a magnetic stirrer to prepare the spraying liquid (concentration of 10% W/V). Next, 400 parts PEO (POLYOX® WSR-303, The Dow Chemical Company) were introduced to a fluid bed granulator (Flow Coater, Freund Industry Co., Ltd.) and sized by spraying the above-mentioned spraying liquid with an inlet temperature of 30° C., spraying speed of 5 g/minute, and spraying/drying/shaking cycle of 20 seconds/30 seconds/10 seconds. After granulation, the sized product was dried for 30 minutes at an inlet temperature of 40° C. to obtain the sized product of the present invention.

EXAMPLE 2

The sized product of the present invention was obtained by the method in Example 1 using 2 parts of Macrogol 60000 and 38 parts of water.

EXAMPLE 3

The sized product of the present invention was obtained by the same manufacturing method as in Example 1 with the PEG being changed to HPMC (6 mPa·s) as the binder.

REFERENCE 1, COMPARATIVE EXAMPLES 1 THROUGH 4

The powder properties of commercial PEO (powder properties of unsized product: Reference) will serve as Reference 1.

A comparative example sized product was obtained by the same method as in Example 1 using water (Comparative Example 1), PVP (Comparative Example 2), sorbitol (Comparative Example 3), and Tween 80 (Comparative Example 4) as the size controlling agent. The properties of the sized products are shown in Table 1.

TABLE 1

| | Example 1 | Example 2 | Example 3 | Comparative Example 1 | Comparative Example 2 | Comparative Example 3 | Comparative Example 4 | Reference 1 |
|---|---|---|---|---|---|---|---|---|
| Size controlling agent | PEG | PEG | HPMC | None (water) | PVP | Sorbitol | Tween80 | Commercial unsized product |
| Weight ratio (%) to PEO | 1.0 | 0.5 | 1.0 | None | 1.0 | 1.0 | 1.0 | |
| Liquid concentration (%) | 10 | 5 | 10 | 10 | 10 | 10 | 10 | |
| Average particle diameter (%) | 136 | 142 | 134 | 176 | 201 | 110 | 114 | 122 |

TABLE 1-continued

|  | Example 1 | Example 2 | Example 3 | Comparative Example 1 | Comparative Example 2 | Comparative Example 3 | Comparative Example 4 | Reference 1 |
| --- | --- | --- | --- | --- | --- | --- | --- | --- |
| Amount of fine powder (%) (<75 μm) | 13.3 | 11.2 | 14.6 | 2.8 | 0.2 | 37.7 | 26.6 | 21.0 |
| Specific volume (mL/g) | 2.72 | 2.92 | 2.75 | 3.42 | 3.19 | 2.42 | 2.26 | 2.27 |
| Angle of repose (°) | 40 | 39 | 37 | 40 | 42 | 39 | 38 | 39 |
| Degree of compression (%) | 8.0 | 12.5 | 10.6 | 20.2 | 15.2 | 7.0 | 10.5 | 11.4 |

<Results and Discussion>

The effects of each type of size controlling agent during aqueous sizing of PEO were studied.

When the commercial PEO product was observed with an electron microscope, the fine particles of about 10 μm had aggregated to form aggregated particles of 50 to 200 μm. When powder properties were-determined, specific volume was 2.3 mL/g, there was approximately 21% fine powder of 75 μ or smaller, and the degree of compression, which is an indicator of fluidity, was 11.4%.

When the PEO was sized by being sprayed with water only without using any size controlling agent whatsoever, granulation proceeded and the amount of fine powder of 75 μm or smaller decreased to approximately 3%. However, the product was bulky (specific volume of 3.4 ml/g) and fluidity was poor with the degree of compression being 20.2%. Electron micrographs revealed particles that had bound together without being broken down into fine particles of uniform size (electron micrographs were not appended).

When PVP was used as the size controlling agent, the particles grew (granulation proceeded) more than when only water was used and as a result, the amount of fine powder of 75 μm or smaller was approximately 0%, specific volume was 3.2 ml/g, and fluidity was poor with the degree of compression being 15.2%. A granulation product was observed in electron micrographs wherein particles that had been broken down were of a uniform size (electron micrographs were not appended).

The amount of fine powder of 75 μm or smaller increased to 38% and 27% with aqueous sorbitol and aqueous polysorbate solutions, respectively. Particles that had been broken down into fine particles were observed in the electron micrographs (electron micrographs were not appended).

Fine powder of the appropriate size that contained 13% and 15% of fine powder of 75 μm or smaller was granulated using aqueous solutions of PEG and HPMC, respectively, without increasing the average particle diameter. Fluidity was also improved over that of the original PEO particles with the degree of compression being 7.7% and 10.6%, respectively. A reduction in fine particles and the formation of particles with a smooth surface of 100 to 200 μm was observed in electron micrographs (electron micrographs were not appended).

<Evaluations>

Granulation usually means a series of unit processes by which particle growth is promoted and decreases fine powder in order to eliminate the problems of adhesion to the punch and scattering of powder during tableting.

When sorbitol and polysorbate are used as the PEO size controlling agent, there is a large amount of fine powder and therefore, these substances are not appropriate.

Sorbitol and polysorbate have a high plasticity and poor binding force and therefore, when they are used as a PEO size controlling agent, it is thought that the PEO particles that have been broken down by spraying with an aqueous solution do not re-bind during drying and cannot be sized.

When PVP is used as the PEO size controlling agent, there is a reduction in fine powder, but a powder of high specific volume and poor fluidity is produced and there are problems in terms of the above-mentioned tableting obstruction and weight uniformity. Therefore, PVP is undesirable.

PVP has poor plasticity and strong binding force and therefore, when used as a PEO size controlling-agent, it is thought the PEO particles that have been broken down into fine particles dry, and granulation to larger particles proceeds.

When PEG or HPMC is used as the PEO size controlling agent, there is a reduction in the amount of fine powder and a sized product of good fluidity is obtained.

PEG and HPMC have the appropriate plasticity and binding force and therefore, it appears that when they are used as a PEO size controlling agent, it is possible that fine PEO particles that have been broken down re-bind and dry in a state of good fluidity and with a smooth surface.

EXAMPLE 4

First, 4-8 parts of Macrogol 6000 were mixed and dissolved in 14.4 parts of water using a magnetic stirrer. Then 0.8 part of tamsulosin hydrochloride that had been pre-pulverizedwith a banner mill (Sample Mill AP-S, using 1 mm screen, Hosokawa Micron Corporation) was suspended (partially dissolved) in this liquid while mixing with a magnetic stirrer to prepare the spraying liquid. Next, 75.2 parts of Macrogol 6000 and 400 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 25° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 94 μm, a specific volume of 2.27 mL/g, and angle of repose of 39° C. Blending uniformity of the drug in the sized product was good with drug content being 97.3% at a standard deviation of 1.2%. After adding and mixing 2.4 parts of magnesium stearate with 480.8 parts of this dry sized product, this mixture was made tableted at a tablet weight of 241.6 mg under a tabletting pressure of 400 kgf/punch from a 9 mm φ punch using a rotary tablet machine (HT P-22, Hata Iron Works, Ltd.) to obtain the controlled-release pharmaceutical preparation (tablets) of the present invention. The tablets that were obtained had few variations with standard deviation of weight being 0.2%.

EXAMPLE 5

First, 4.8 parts of Macrogol 6000 were mixed and dissolved in 14.2 parts of water using a magnetic stirrer. Then 1.0 part of tamsulosin hydrochloride that had been pre-pulverized with a hammer mill (Sample Mill AP-S, using 1 mm screen, Hosokawa Micron Corporation) was suspended (partially dissolved) in this liquid while mixing with a magnetic stirrer to prepare the spraying liquid. Next, 70.2 parts of Macrogol 6000 and 375 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 25° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 93 μm, a specific volume of 2.22 ml/g, and angle of repose of 39°. Blending uniformity of the drug in the sized product was good with drug content being 97.7% at a standard deviation of 0.7%. After adding and mixing 2.25 parts of magnesium stearate with 451 parts of this dry sized product, this mixture was made tableted at a tablet weight of 181.3 mg under a tabletting pressure of 400 kgf/punch from a 7.5 mm φ punch using a rotary tablet machine (HIT P-22, Hata Iron Works, Ltd.) to obtain the controlled-release pharmaceutical preparation (tablets) of the present invention. The tablets that were obtained had few variations with standard deviation of weight being 0.4%.

EXAMPLE 6

First, 3.84 parts of Macrogol 6000 were mixed and dissolved in 9.76 parts of water using a magnetic stirrer. Then 2.4 parts of tamsulosin hydrochloride that had been pre-pulverized with a hammer mill (Sample Mill AP-S, using 1 mm screen, Hosokawa Micron Corporation) were suspended in this liquid while mixing with a magnetic stirrer to prepare the spraying liquid. Next, 76.16 parts of Macrogol 6000 and 400 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 25° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product bad an average particle diameter of 100 μm, a specific volume of 2.38 mL/g, and angle of repose of 38°. After adding and mixing 2.4 parts of magnesium stearate with 482.4 parts of this dry sized product, this mixture was made tableted at a tablet weight of 242.4 mg under a tabletting pressure of 400 kgf/punch from a 9 mm φ punch using a rotary tablet machine (HT P-22, Hata Iron Works, Ltd.) to obtain the controlled-release pharmaceutical preparation (tablets) of the present invention. The tablets that were obtained had few variations with standard deviation of weight being 0.6%, and uniformity of content was also good at a standard deviation of 1.0%.

EXAMPLE 7

First, 4.8 parts of Macrogol 6000 were mixed and dissolved in 14.4 parts of water using a magnetic stirrer. Then 0.8 part of tamsulosin hydrochloride that had been pre-pulverized with a hammer mill (Sample Mill AP-S, using 1 mm screen, Hosokawa Micron Corporation) was suspended in this liquid while mixing with a magnetic stirrer to prepare the spraying liquid. Next, 75.2 parts of Macrogol 6000 and 400 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 30° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 106 μn, a specific volume of 2.33 mL/g, and angle of repose of 36°. After adding and mixing 2.4 parts of magnesium stearate with 480.8 parts of this dry sized product, this mixture was made tableted at a tablet weight of 241.6 mg under a tabletting pressure of 400 kgf/punch from a 9 min φ punch using a rotary tablet machine (HT P-22, Hata Iron Works, Ltd.). The tablets that were obtained had few variations with standard deviation of weight being 0.5%. The tablets were further spray coated with a liquid in which 5.04 parts of hydroxypropylmethyl cellulose (TC-5R, Shin-Etsu Chemical Co., Ltd.), 0.95 part of Macrogol 6000, and 1.26 parts of yellow ferric oxide had been dissolved/dispersed a tan inlet temperature of 60° C., pan rotating speed of 13 rpm, and coating liquid feed speed of 5 g/minute using an aeration-type coating device (Hi-Coater HCT-30, Freund Industry Co., Ltd.) until the coating component was 3% of the tablet weight to obtain the controlled-release pharmaceutical preparation (film-coated tablets) of the present invention. When the film-coated tablets that were obtained were observed microscopically, there was uniform distribution of the coloring matter and the surface was smooth and gelation of the PEO was not seen.

EXAMPLE 8

First, 1.2 parts of tamsulosin hydrochloride were dissolved in 148.8 parts of water to prepare the spraying liquid. Next, 60 parts of Macrogol 6000 and 300 parts of PEO (POLYOX®-WSR, The Dow Chemical Company) were introduced to a fluidized bed granulator (FLOW COATER, Freund Industry Co., Ltd.) and sizing was performed by spraying the above-mentioned spraying liquid at an inlet temperature of 30° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 108 μm, a specific volume of 2.66 mL/g, and angle of repose of 40°. After adding and mixing 1.8 parts of magnesium stearate with this dry sized product, this mixture was made tableted at a tablet weight of 121 mg under a tabletting pressure of 400 kgf/punch from a 7.0 mm φ punch using a rotary tablet machine (HT P-22, Hata Iron Works, Ltd.) to obtain the controlled-release pharmaceutical preparation (tablets) of the present invention. The tablets that were obtained had few variations with standard deviation of weight being 0.6%. Moreover, the drug content of the tablets was 97.8% and uniformity of content was good at a standard deviation of 1.4%.

EXAMPLE 9

First, 2.0 parts of hydroxypropylmethyl cellulose (6 mPa·s) were mixed and dissolved in 18.0 parts of water using a magnetic stirrer. Then 0.8 part of tamsulosin hydrochloride that had been pre-pulverized with a hammer mill (Sample Mill AP-S, using 1 mm screen, Hosokawa Micron Corporation) was suspended (partially dissolved) in this liquid while mixing with a magnetic stirrer to prepare the spraying liquid. Next, 78.0 parts of Macrogol 6000 and 400 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 30° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 95 μm, a specific volume of 2.53 mL/g, and angle of repose of 360. Blending uniformity of the drug in the sized product was good with drug content being 101.6% at a standard deviation of 1.4%.

EXAMPLE 10

First, 3.84 parts of Macrogol 6000 were mixed and dissolved in 10.56 parts of water using a magnetic stirrer. Then 1.6 parts of tamsulosin hydrochloride that had been pre-pulverized with a hammer mill (Sample Mill AP-S, using 1 mm screen, Hosokawa Micron Corporation) were suspended in this liquid while being mixed with a magnetic stirrer to prepare the spraying liquid. Next, 76.16 parts of Macrogol 6000 and 400 parts of PEO (POLYOX® WSR-303, The Dow Chemical Company) were introduced to a fluidized bed granulator (FLOW COATER, Freund industry Co., Ltd.) and sizing was performed by spraying the above-mentioned spraying liquid at an inlet temperature of 25° C., spraying speed of 5 g/minute and spray/dry cycle of 20 seconds/40 seconds. After sizing, the sized product was dried for 30 minutes at an inlet temperature of 40° C. to obtain the sized product of the present invention. The sized product had an average particle diameter of 96 μm, a specific volume of 2.27 mL/g, and angle of repose of 37°. After adding and mixing 2.4 parts of magnesium stearate with 481.6 parts of this dry sized product, this mixture was made tableted at a tablet weight of 242 mg under a tableting pressure of 400 kgf/punch from a 9 mm φ punch using a rotary tablet machine (HT P-22, Hata Iron Works, Ltd.) to obtain the controlled-release pharmaceutical preparation (tablets) of the present invention. The tablets that were obtained had few variations with standard deviation of weight being 0.6%, and uniformity of content was also good at a standard deviation of 1.8%.

COMPARATIVE EXAMPLE 5

After coarse mixing of 10 parts of tamsulosin hydrochloride and 190 parts of Macrogol 6000 with a poly bag, the mixture was pulverized with a hammer mill (Sample Mill AP-S, using 1 mm screen, Hosokawa Micron Corporation). Then 84.8 parts of Macrogol 6000 and 500 parts of PEO (POLYOX® WSR-303, The Dow Chemical Company) were added to 16 parts of the mixed and pulverized product and this was mixed for 10 minutes at 25 rpm using a double cone-type mixer (5 L-type, Tokuju Corporation). Then 3.0 parts of magnesium stearate were further added and mixed to obtain a comparative pharmaceutical preparation of the present invention. When uniformity of drug content of the mixed product that was obtained was confirmed, there was a reduction in drug content at 91.5% and a standard deviation of 1.4%.

COMPARATIVE EXAMPLE 6

First, 3.84 parts of sorbitol were dissolved in 11.36 parts of water while mixing with a magnetic stirrer Then 0.8 part of tamsulosin hydrochloride that had been pre-pulverized with a hammer mill (Sample Mill AP-S, using 1 mm screen, Hosokawa Micron Corporation) were suspended in this liquid while being mixed with a magnetic stirrer to prepare the spraying liquid. Next, 76.16 parts of sorbitol and 400 parts of PEO (POLYOX® WSR-303, The Dow Chemical Company) were introduced to a fluidized bed granulator (FLOW COATER, Freund Industry Co., Ltd.) and sizing was performed by spraying the above-mentioned spraying liquid at an inlet temperature of 30° C., spraying speed of 5 g/minute and spray/dry cycle of 20 seconds/40 seconds. After sizing, the size dproduct was dried for 30 minutes at an inlet temperature of 40° C. to obtain the sized product of the present invention. The sized product had an average particle diameter of 110 μm, a specific volume of 2.04 mL/g, and angle of repose of 38°. Blending uniformity of the drug in the sized product revealed a reduced uniformity of content at a drug content of 98.2% and standard deviation of 5.4%.

INDUSTRIAL APPLICABILITY

The present invention presents a controlled-release pharmaceutical composition containing a sized product, which contains a drug, polyethylene oxide of high viscosity and specific PEO size controlling agent and wherein of-these three components, at least the size controlling agent is uniformly dispersed in the polyethylene oxide.

By means of the present invention, it is possible to present a controlled-release pharmaceutical composition for oral use with good uniformity of content, particularly for low-dose drugs, and therefore, it can be used as useful pharmaceutical preparation technology that is extremely popular, particularly for controlled-release pharmaceutical compositions comprising polyethylene oxide of a high viscosity as the controlled-release base.

The invention claimed is:

1. A pharmaceutical composition for controlled release comprising a sized product, which comprises
   (a) a drug, wherein said drug is present at 10% w/w or less;
   (b) a polyethylene oxide with a viscosity-average molecular weight of 2,000,000 or more;
   (c) a size controlling agent, wherein said size controlling agent is one or two or more selected from the group consisting of polyethylene glycol that is solid at ordinary temperature, hydroxypropylmethyl cellulose of 2 to 15 mPa·s (2% w/v), hydroxypropyl cellulose of 2 to 10 mPa·s (2% w/v), and methyl cellulose of 2 to 15 mPa·s (2% w/v), wherein said drug, and said size controlling agent are sprayed as an aqueous solution or as a suspension onto said polyethylene oxide to form a sized product; and wherein said sized product is a collection of particles wherein the average diameter of said particles is approximately 60 to 300 μm and wherein the specific volume of said particles is 2.0 to 3.0 ml/g.

2. The pharmaceutical composition for controlled release according to claim 1, wherein the amount of size controlling agent (c) is 0.5 to 60 wt % per polyethylene oxide (b).

3. The pharmaceutical composition for controlled release according to claim 1, wherein when polyethylene glycol is selected as size controlling agent (c), the amount is 0.5 to 60 wt % per unit of the pharmaceutical preparation.

4. The pharmaceutical composition for controlled release according to claim 1, wherein the amount of polyethylene oxide (b) is 10 to 95 wt % per unit of the pharmaceutical preparation.

5. The pharmaceutical composition for controlled release according to claim 1, wherein the amount of polyethylene oxide (b) added is at least 70 mg per unit of the pharmaceutical preparation.

6. The pharmaceutical composition for controlled release according to claim 1, wherein the viscosity-average molecular weight of polyethylene oxide (b) is 5,000,000 or higher.

7. The pharmaceutical composition for controlled release according to claim 1, which further comprises a hydrophilic base.

8. The pharmaceutical composition for controlled release according to claim 7, wherein the amount of water required to dissolve 1 g of said base is 5 ml or less (20±5° C.).

9. The pharmaceutical composition for controlled release according to claim 8, wherein the hydrophilic baseis polyethylene glycol, sucrose, orpolyvinyl pyrrolidone.

10. The pharmaceutical composition for controlled release according to claim 7, wherein the amount of hydrophilic base is 5 to 80 wt % per unit of the pharmaceutical preparation.

11. The pharmaceutical composition for controlled release according to claim 1, which further comprises yellow ferric oxide and/or red ferric oxide.

12. The pharmaceutical composition for controlled release according to claim 11, wherein the amount of yellow ferric oxide and/or ferric oxide is 0.3 to 20 wt % per polyethylene oxide.

13. The pharmaceutical composition for controlled release according to claim 1, wherein the amount of drug is 85 wt % or less per unit of the pharmaceutical preparation.

14. The pharmaceutical composition for controlled release according to claim 1, wherein the drug is tamsulosin hydrochloride.

15. The pharmaceutical composition for controlled release according to claim 1, which comprises essentially no organic solvent.

16. A polyethylene oxide-containing sized product for controlled release pharmaceutical compositions, which contains polyethylene oxide (b) with a viscosity-average molecular weight of 2,000,000 or more and a size controlling agent uniformly dispersed in said polyethylene oxide, wherein said size controlling agent is one or two or more selected from the group consisting of polyethylene glycol that is solid at ordinary temperature, hydroxypropylmethyl cellulose of 2 to 15 mPa·s (2% w/v), hydroxypropyl cellulose of 2 to 10 mPa·s (2% w/v), and methyl cellulose of 2 to 15 mPa·s (2% w/v), sprayed as an aqueous solution; and wherein said sized product is a collection of particles wherein the average diameter of said particles is approximately 60 to 300 μm and wherein the specific volume of said particles is 2.0 to 3.0 ml/g.

17. The sized product according to claim 16, which further comprises a drug.

18. The sized product according to claim 16, wherein the amount of drug is 85 wt % or less per unit of the pharmaceutical preparation.

19. The sized product according to claim 18, wherein the amount of drug is 10 wt % or less per unit of the pharmaceutical preparation.

20. The sized product according to claim 16, wherein the drug is tamsulosin hydrochloride.

21. The sized product according to claim 16, which comprises essentially no organic solvent.

22. A pharmaceutical composition for controlled release comprising a sized product, which comprises
(a) a drug, wherein the drug is tamsulosin or a pharmaceutically acceptable salt, which is present at 10% w/w or less;
(b) a polyethylene oxide with a viscosity-average molecular weight of 2,000,000 or more;
(c) a size controlling agent, wherein said size controlling agent is one or two or more selected from the group consisting of polyethylene glycol that is solid at ordinary temperature, hydroxypropylmethyl cellulose of 2 to 15 mPa·s (2% w/v), hydroxypropyl cellulose of 2 to 10 mPa·s (2% w/v), and methyl cellulose of 2 to 15 mPa·s (2% w/v), wherein said drug, and said size controlling agent are sprayed as an aqueous solution or as a suspension onto said polyethylene oxide to form a sized product; and wherein said sized product is a collection of particles wherein the average diameter of said particles is approximately 60 to 300 μm and wherein the specific volume of said particles is 2.0 to 3.0 ml/g.

23. The pharmaceutical composition for controlled release according to claim 22, which further comprises a hydrophilic base.

24. The pharmaceutical composition for controlled release according to claim 23, wherein the amount of water required to dissolve 1 g of said base is 5 ml or less (20±5° C.).

25. The pharmaceutical composition for controlled release according to claim 24, wherein the hydrophilic base is polyethylene glycol, sucrose, or polyvinyl pyrrolidone.

26. The pharmaceutical composition for controlled release according to claim 23, wherein the amount of hydrophilic base is 5 to 80 wt % per unit of the pharmaceutical preparation.

27. The pharmaceutical composition for controlled release according to claim 22, which further comprises yellow ferric oxide and/or red ferric oxide.

28. The pharmaceutical composition for controlled release according to claim 27, wherein the amount of yellow ferric oxide and/or ferric oxide is 0.3 to 20 wt % per polyethylene oxide.

29. The pharmaceutical composition for controlled release according to claim 22, wherein the amount of drug is 85 wt % or less per unit of the pharmaceutical preparation.

30. The pharmaceutical composition for controlled release according to claim 22, wherein the drug is tamsulosin hydrochloride.

31. A pharmaceutical composition for controlled release comprising a sized product, which comprises
(a) a drug, wherein the drug is tamsulosin hydrochloride, which is present at 10% w/w or less;
(b) a polyethylene oxide with a viscosity-average molecular weight of 2,000,000 or more;
(c) a size controlling agent, wherein said size controlling agent is polyethylene glycol, wherein said drug and said size controlling agent are sprayed as an aqueous solution or as a suspension onto said polyethylene oxide to form a sized product; and wherein said sized product is a collection of particles wherein the average diameter of said particles is approximately 60 to 300 μm and wherein the specific volume of said particles is 2.0 to 3.0 ml/g.

* * * * *